United States Patent [19]

Lacroix

[11] Patent Number: 4,921,991

[45] Date of Patent: May 1, 1990

[54] PREPARATION OF ESTERS OF THE N-PHOSPHONOMETHYLGLYCINE AND THE N-PHOSPHONOMETHYL GLYCINES

[76] Inventor: Guy Lacroix, 332 F Balmont-Law Duchére, 69009 - Lyon, France

[21] Appl. No.: 947,980

[22] Filed: Dec. 31, 1986

Related U.S. Application Data

[60] Division of Ser. No. 704,239, Feb. 22, 1985, abandoned, which is a continuation-in-part of Ser. No. 635,225, Jul. 27, 1984, abandoned.

[51] Int. Cl.$^5$ .............................. C07F 9/38; C07F 9/40
[52] U.S. Cl. ...................................... 558/135; 558/169
[58] Field of Search ................................ 558/135, 169

[56] References Cited

U.S. PATENT DOCUMENTS

| | | | |
|---|---|---|---|
| 3,288,846 | 11/1966 | Irani | 562/11 |
| 3,835,000 | 9/1974 | Frazier et al. | 558/169 |
| 3,927,080 | 12/1975 | Gaertner | 562/11 |
| 4,062,669 | 12/1977 | Franz | 71/86 |
| 4,422,982 | 12/1983 | Subramanion | 562/11 |
| 4,439,373 | 3/1984 | Nagubandi | 260/941 |
| 4,491,548 | 1/1985 | Nagubandi | 558/135 |

*Primary Examiner*—Anton H. Sutto
*Attorney, Agent, or Firm*—Morgan & Finnegan

[57] ABSTRACT

Phosphonic diesters, capable of being employed as intermediates for making herbicides, having the formula

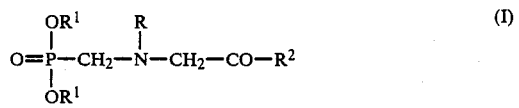

in which R denotes a hydrogenolyzable group; preferably an arylalkyl group, $R^1$ denotes a hydrolyzable group, $R^2$ denotes a hydrogen atom or hydrolyzable group such as those defined for $R^1$.

Preparation of the compounds of the formula (I) from phosphites, formaldehyde and N-substituted glycine esters.

19 Claims, No Drawings

PREPARATION OF ESTERS OF THE N-PHOSPHONOMETHYLGLYCINE AND THE N-PHOSPHONOMETHYL GLYCINES

This is a divisional of co-pending application Ser. No. 704,239 filed Feb. 22, 1985, which is a continuation-in-part of U.S. patent application Ser. No. 635,225 filed Jul. 27, 1984, both now abandoned which claims convention priority to French applications Nos. 84.02988 and 83.12620 filed Feb. 23, 1984 and Jul. 27, 1983, respectively. The present application also claims priority to French application No. 84.02988 and the entirety of U.S. Ser. No. 635,255 and said French applications are incorporated herein by reference.

The present invention relates to N-substituted phosphonic esters of the N-phosphonomethylglycine family and to their preparation and their use for the synthesis of herbicides.

Numerous herbicides belonging to the N-phosphonomethylglycine family are known (U.S. Pat. Nos. 3,455,675, 4,388,103 and 4,397,676, French Pat. No. 2,129,327, European Pat. Nos. 53,871, 54,382, 73,574a, PCT No. WO83/03,608, British Pat. No. 2,090,596, and Belgian Pat. Nos. 894,244, 894,245, 894,590, 894,591, 894,592, 894,593, 894,594, and 894,595). The invention is directed to providing intermediate compounds and processes for preparing herbicidal compounds of this family.

The invention aims at providing a very simple and improved process for preparing herbicides, which employs relatively simple reactants, particularly glycine and its simple derivatives.

Other aims and benefits of the invention will become apparent in the course of the description which follows.

Mention has already been made to French Pat. No. 2,129,327 which describes the formation of triesters of N-phosphonomethylglycine by the reaction of ethyl glycinate with formaldehyde and with diethyl phosphite. This process is unsatisfactory, since it is believed to be excessively directed towards the formation of N,N-bis(phosphonomethyl)glycine. For this reason it has been proposed in French Pat. No. 2,193,830 to prepare N-phosphonomethylglycine by reacting an N-arylalkylglycine with formaldehyde and phosphorous acid with subsequent elimination of the N-arylalkyl group by the action of hydrobromic or hydriodic acid. However, this process is also not considered to be satisfactory because of the low yields obtained and because of the formation of lachrymatory benzyl bromide.

It has also been proposed to prepare N-phosphonomethylglycine by the reaction of N-substituted glycine with formaldehyde and with phosphorous acid, followed by a hydrogenolysis of the (N,N-disubstituted) N-phosphonomethylglycine which is obtained. This process has the disadvantage of being carried out in a very dilute medium and in having a very long reaction time. As a result, as illustrated by European Pat. No. 81,459, there has been a move toward the use of reactants other than glycine and formaldehyde in such synthesis processes. For example, it has been suggested to react aminomethylphosphonic acid with glyoxal in the presence of $SO_2$.

It has now been discovered, and this is the subject of the present invention, that herbicides of the N-phosphonomethylglycine family can be obtained by virtue of new intermediate products, which are themselves accessible from N-substituted glycine esters and formaldehyde.

More precisely, the invention relates to phosphonic diesters of the formula:

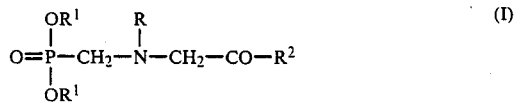

in which
R denotes a hydrogenolyzable group, preferably an arylalkyl group,
$R^1$ denotes a hydrolyzable group,
$R^2$ denotes a hydrogen atom or hydrolyzable group such as those defined for $R^1$.

The radical R may, in particular, be a radical of the formula:

in which
Ar is an aromatic group, such as phenyl or naphthyl, phenyl being preferred; this radical Ar may, if desired, carry one or more substituents which do not interfere with the reactions involved in the process (e.g. alkyl, alkoxy, nitro and others, the number of carbon atoms being preferably not more than 6), although it does not appear particularly advantageous to employ such substituents,
$R^3$ and $R^4$ according to Formula II denote the hydrogen atom or a radical Ar or an alkyl group, said alkyl preferably containing up to 6 carbon atoms.

Illustrative radicals R which may be mentioned are benzyl, 1-phenylethyl, 1-phenylpropyl, naphthylmethyl, 1-naphthylethyl, 1-naphthylpropyl, diphenylmethyl, and trityl (=triphenylmethyl) radicals.

$R^1$ is such that $OR^1$ is a hydrolyzable radical. Examples of hydrolyzable radicals which may be mentioned are optionally substituted hydrocarbyl radicals, particularly alkyl, cycloalkyl or phenyl radicals, each of which may be optionally substituted by halogen atoms (e.g. chlorine or fluorine) or by phenyl, cyano, alkoxyl, alktoxycarbonyl or alkylcarboxylate groups. $R^1$ generally contains up to 12 carbon atoms and preferably from 1 to 8 carbon atoms. $R^1$ is advantageously an alkyl radical containing from 1 to 6 carbon atoms.

Preparation of the compounds of the formula (I) is conveniently carried out by the reaction of a phosphite (or phosphonic ester) of the formula:

with formaldehyde and an N-substituted derivative of glycine, the substituent on the nitrogen atom being a hydrogenolyzable substituent; this N-substituted glycine derivative is in practice a compound of the formula $R-NH-CH_2-CO-O-R^2$.

The reaction is generally carried out between 0° and 100° C., preferably between 20° and 90° C. by mixing the reactants. Although a large excess (3/1 to 1/3 in molar ratios) of one of the reactants relative to the other is possible, in practice more advantageous to operate as close to stoichiometry as possible and not to depart by more than about 20 mole % from this stoichiometry. It is indeed one of the major advantages of the invention not to require an excess of one of the reactants relative to the others. Another advantage of the invention lies in the good yields obtained in the preparation of the compounds according to the invention.

Formaldehyde is employed in any of the conveniently accessible forms. According to a preferred method it is employed in the form of an aqueous solution of a concentration between 1% and saturation, preferably of 30 to 40%.

The reaction may be carried out in the presence of an inert solvent, but generally such a solvent is unnecessary and it is indeed another advantage of the invention not to require a solvent for the preparation of the compounds of formula (I) (except for the water present in the aqueous solution of formaldehyde, formalin, according to a preferred method).

The reaction product is isolated by any means known per se.

The compounds of the formula (I) may be converted into known herbicidal products of the formula:

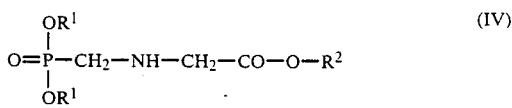

by simple hydrogenolysis of the group R. In most cases this is a debenzylation reaction. It is carried out advantageously in an aqueous or alcoholic medium at ambient or elevated temperature, and at atmospheric pressure or above. The usual catalysts of hydrogenolysis of the radicals R in question may be employed as a catalyst. Suitable catalysts which may be mentioned are palladium, platinum, and Raney nickel. This catalyst may be employed with or without an inert support. It is also possible to employ the abovementioned metals, particularly palladium and platinum, in the form of salts, hydroxides, or oxides, which are converted to the corresponding metal under the action of hydrogen. Palladium-based catalysts, such as palladium on charcoal or palladium on barium sulphate, or palladium hydroxide on charcoal, are employed as a preferred debenzylation catalyst. At the end of the reaction, the catalyst may be separated by filtration and the filtrate evaporated; this yields the products of the formula (IV) in a substantially pure state. A major advantage of the invention lies in the fact that the reaction time for this debenzylation is relatively short, which makes it possible to use reduced quantities of catalyst.

In order to prepare non-esterified herbicidal compounds, such as for example N-phosphonomethylglycine itself, the product of the formula (IV) may be hydrolyzed completely or partially in a known manner, e.g. by heating said product with an aqueous solution of an acid or alkaline agent, particulary a hydroxide or carbonate of an alkali-metal or alkaline-earth metal, or a strong inorganic or organic acid, such as hydrochloric, sulphuric, phosphoric, perchloric or arylsulphonic acids. This hydrolysis may also be accompanied by a salt formation or a conversion of other herbicidal derivatives.

The following examples, which are given without implying a limitation, illustrate the invention and show how it can be used in practice.

EXAMPLE 1

This Example illustrates the preparation of the triester, Ethyl-N-benzyl-N-(diethylphosphonomethyl) glycinate.

An aqueous solution (440 g) containing 30% by weight of formaldehyde (14.66 moles) is poured, with stirring, at ambient temperature, over 1 h 30 min, into a mixture of ethyl N Benzylglycinate (2,830 g; 14.66 moles) and diethyl phosphite [$(C_2H_5))_2P(O)H$] (2,028 g; 14.17 moles). During the pouring the temperature rises up to 41° C. The mixture is heated for 1 h 30 min at 90° C., and then cooled.

To extract the reaction product, $CH_2Cl_2$ (7 l) is added and the material is washed with water (3×6 l). The solvent is removed. A light brown oil (4,647 g) with a refractive index $n_D^{20}$ of 1.491 is thus obtained. The yield is 92.4%. The product obtained has the formula:

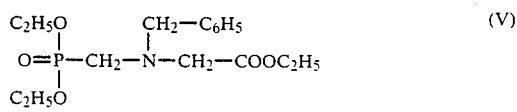

EXAMPLE 2

The procedure in Example 1 is followed except that diethyl phosphite is replaced with dimethyl phosphite or methyl phosphonate, of the formula $(CH_3O)_2P(O)H$.

The compound of the formula:

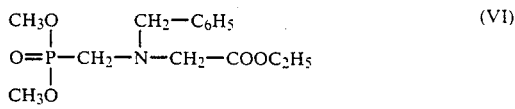

is obtained in 87% yield: its refractive index $n_D^{20}$ is 1.499.

EXAMPLE 3

An aqueous solution containing 5% by weight of sodium hydroxide (6.8 l) is poured at 40° C., over 1½ h, into the compound of the formula (V) (2,915 g). The mixture is then heated at 80° C. for 1½ h, cooled and washed with $CH_2Cl_2$ (4 l). The aqueous solution is acidified to pH 2 with 10N hydrochloric acid (800 ml). The product separates from the aqueous layer in the form of an oil which is extracted with $CH_2Cl_2$ (5 l). The methylene chloride solution is washed with water (2×2.5 l). It is evaporated to dryness and the product of the formula

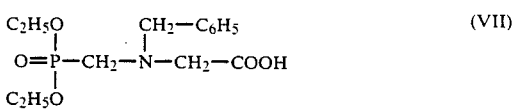

(2,012 g; 75% yield), which crystallizes on storage (m.p.: 37° C.) is thus obtained.

EXAMPLE 4

The procedure is as in Example 3, the product of the formula (VI) being employed in place of the compound of the formula (V) as starting material. The product of the formula

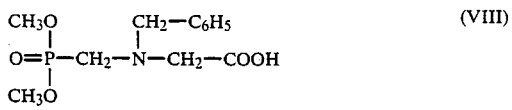

which melts at 73.8° C. is thus obtained in 36% yield.

EXAMPLE 5

A solution of the compound of the formula (V) (68.6 g) in methanol (150 ml) is charged into a 500-ml reactor. A paste made with water (10 ml) and activated charcoal containing 10% by weight of palladium (9 g) is added. The atmosphere is purged with nitrogen and then hydrogen is circulated for 5 h at 20° C. The material is filtered, the filtrate is evaporated and the product of the formula

(49 g; 97% yield) is thus obtained in the form of a liquid with a refractive index $n_D^{20}$ of 1.451. This compound of the formula (IX) (12.7 g) is dissolved in an aqueous solution (50 ml) containing 20% by weight of hydrochloric acid. The solution is boiled under reflux for 20 h. It is concentrated under reduced pressure, and the residue washed with methanol. After drying, N-phosphonomethylglycine (6.5 g; 77% yield) is obtained.

EXAMPLE 6

The compound of the formula (VII) (10 g) is dissolved in methanol (50 ml) in a 250-ml reactor. The catalyst paste employed in Example 5 (0.3 g) is added. The atmosphere is purged with nitrogen, and hydrogen is then circulated for 2 h at ambient temperature (20° to 25° C.). The material is filtered, the filtrate evaporated and the product of the formula

(7.5 g; 100% yield) is obtained. After recrystallization the product melts at 115° C.

EXAMPLE 7

N-Benzylglycine (39 g), water (80 ml) and an aqueous solution (20.3 ml) of formaldehyde (0.248 mole) are mixed. Diphenylphoshite $(C_6H_5O)_2PH(O)$ (58 g=0.248 mole) is added dropwise at ambient temperature. After 30 minutes, the temperature is allowed to rise to 30° and stirring is continued for one hour. The product is filtered off, washed with water and dried. After recrystallization from a mixture of isopropyl ether and isopropanol in the ratio of 10/1 by volume, a white powder (57.4 g) is obtained (yield 59.1%), which melts at 91° and consists of the product of the formula:

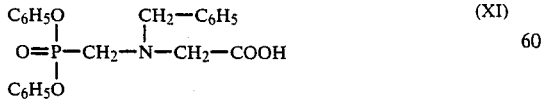

EXAMPLE 8

N-Benzylglycine (16.5 g), water (28 ml) and diethylphosphite $(C_2H_5O)_2PH(O)$ (13.8 g) are mixed. An aqueous 37% strength formaldehyde solution (9 ml=0.11 mole) is added at 20° C. No exothermic effect is observed. The mixture is heated for five hours at 50° and then cooled, and $CH_2Cl_2$ (40 ml) is added. The organic phase is separated off and water (40 ml) followed by N aqueous NaOH solution (100 ml) are added. The aqueous phase is decanted, extracted with $CH_2Cl_2$ and acidified. The organic phase is dried and evaporated. A product (23.5 g=74% yield) is obtained of the formula:

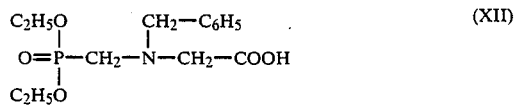

EXAMPLE 9

Ethyl N-benzlglycinate is saponified in situ. An aqueous 30% strength NaOH solution (0.5 l=5 moles) and water (1 l) are mixed into this solution, ethyl N-benzylglycinate (965 g) is poured gradually over one hour. The temperature rises to 45° C. The ethanol is distilled off, the residue is cooled and a 6N aqueous hydrochloric acid solution (0.82 l) is added. The N-benzylglycine precipitates. Diethylphosphite (690 g) and 37% strength aqueous formaldehyde (0.45 l=5 moles) are added. The mixture is heated for 5 hours 30 minutes at 50° C. Thereafter the procedure of Example 2 is followed. The product of formula (XII) (1116 g=71% yield) is obtained.

I claim:

1. A phosphonic ester having the formula

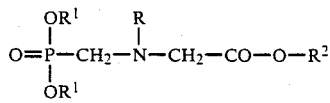

in which
R denotes an arylalkyl group,
R' is selected from the alkyl and aryl groups of 1 to 12 carbon atoms which are opionally substituted by one or more of the groups halogen, phenyl, cyano, alkoxy, and alkylcarboxylate,
$R^2$ denotes a hydrogen or $R^1$.

2. A compound according to claim 1 wherein $R^1$ is an optionally substituted alkyl group.

3. A compound according to claim 1 wherein $R^1$ is an optionally substituted aryl group.

4. A compound according to claim 2 wherein $R^1$ is an unsubstituted alkyl group of 1 to 8 carbon atoms.

5. A compound according to claim 1, in which the radical R is a radical of the formula:

in which
Ar is an optionally substituted aromatic group selected from phenyl and naphthyl,
$R^3$ and $R^4$ denote a hydrogen atom or Ar or an alkyl group of 1 to 6 carbon atoms.

6. A compound according to claim 1, in which R is a benzyl radical.

7. A compound according to claim 1 wherein $R^1$ and $R^2$ are unsubstituted alkyl radicals of 1 to 6 carbon atoms.

8. A compound according to claim 6 wherein R is a benzyl radical.

9. A phosphonic ester having the formula

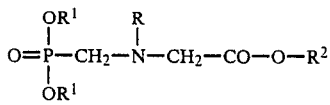

in which
R denotes an arylalkyl group,
$R^1$ and $R^2$ are selected from alkyl and aryl groups of 1 to 12 carbon atoms which are optionally substituted by one or more of the groups halogen, phenyl, cyano, alkoxy and alkylcarboxylate.

10. A compound according to claim 1, in which $R^2$ is selected from optionally substituted alkyl and phenyl radicals of 1 to 12 carbon atoms.

11. A compound according to claim 10, in which $R^2$ is an optionally substituted alkyl radical containing from 1 to 6 carbon atoms.

12. A compound according to claim 10 wherein $R^2$ is hydrogen.

13. A compound which is Ethyl-N-benzyl-N-diethyl-phosphonomethyl-glycinate.

14. A compound which is Ethyl-N-benzyl-N-dimethylphosphonomethyl-glycinate.

15. A process for preparing compounds according to claim 1, in which a phosphonic ester of the formula $(R^1O)_2P(O)H$ is reacted with formaldehyde and a compound of the formula $R-NH-CH_2-COOR^2$.

16. A process according to claim 15, in which the reaction is carried out between 0° and 100° C.

17. The process according to claim 16 wherein each reactant is in a proportion which does not depart from stoichiometry by more than about 20%.

18. A process according to claim 15, wherein the radical R is a radical of the formula:

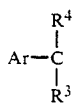

in which
Ar is an optionally substituted aromatic group and
$R^3$ and $R^4$ each represent a hydrogen atom or a radical Ar or an alkyl group of 1 to 6 carbon atoms.

19. A process according to claim 18, in which R is a benzyl radical.

* * * * *